(12) United States Patent
Kotani et al.

(10) Patent No.: US 6,863,907 B2
(45) Date of Patent: Mar. 8, 2005

(54) ANTIALLERGIC COMPOSITION AND ANTIPRURITIC COMPOSITION

(75) Inventors: Mayumi Kotani, Kobe (JP); Akihito Fujita, Takatsuki (JP); Motonobu Matsumoto, Takatsuki (JP)

(73) Assignees: Sunstar, Inc., Osaka-Fu (JP); Uni-Sunstar B.V., Amsterdam (NL)

( * ) Notice: Subject to any disclaimer, the term of this patent is extended or adjusted under 35 U.S.C. 154(b) by 651 days.

(21) Appl. No.: 09/504,914

(22) Filed: Feb. 16, 2000

(65) Prior Publication Data

US 2002/0009503 A1 Jan. 24, 2002

(30) Foreign Application Priority Data

Feb. 16, 1999 (JP) ............................................. 11-037767

(51) Int. Cl.$^7$ ...................... A61K 35/78; A61K 47/00
(52) U.S. Cl. ...................... 424/771; 424/439; 514/861; 514/863
(58) Field of Search ................................ 424/725, 771; 424/439; 514/861, 863

(56) References Cited

U.S. PATENT DOCUMENTS

| | | | | |
|---|---|---|---|---|
| 4,683,140 A | * | 7/1987 | Kang | |
| 5,098,709 A | * | 3/1992 | Kang | |
| 5,221,289 A | * | 6/1993 | Miyamatsu | |
| 5,723,139 A | * | 3/1998 | Granger et al. | |

FOREIGN PATENT DOCUMENTS

| | | | |
|---|---|---|---|
| CN | 1091951 | * | 9/1994 |
| CN | 1225268 | * | 9/1994 |
| CN | 1225268 | * | 8/1999 |
| EP | 0 543 051 | | 5/1993 |
| JP | 57144226 A | * | 9/1982 |
| JP | 03291233 A | * | 12/1991 |
| JP | 04 169535 | | 6/1992 |
| JP | 08211731 A | * | 8/1996 |
| WO | 0543051 | * | 11/1991 |

OTHER PUBLICATIONS

Food Sci. Technol. Int. Tokyo, 3(2): 179–183. (1997). Yamada et al. Effect of tea extracts & phenolic components on immunoglobulin production by mesenteric lymph node lymphocytes of Sprague–Dawley rats.*
Park et al. Han'guk Sikp'um Yongyang Kwahak Hoechi. 29(1), 111–115. Effect of polyphenol compounds from persimmon leaves (Diospyros kaki folium) on allergic contact dermatitis, Jan. 2000.*
Berkow, R. et al., The Merck Manual of Manual Information: Home Edition, Merck & Co., Inc., pp. 203, 901–910, 1048–1057, and 1063–1065, 1997.*
Yamada et al., Food Sci. Technol. Int. Tokyo, 3(2):179–183. Effect of tea extracts & phenolic components on immunoglobulin production by mesenteric lymph node lymphocytes of Sprague–Dawley rats, 1997.*
Osaka Prefectural Institute of Public Health Report Edited by Pharmaceutical Affairs Department (No. 29, 1995) pp. 1–5.
Kotani et al, *Nippon Eiyo Shokuryo Gakkashi*, 52(3):147–151 (1999)—Abstract.

* cited by examiner

Primary Examiner—Christopher R. Tate
Assistant Examiner—Michele C. Flood
(74) Attorney, Agent, or Firm—Sughrue Mion, PLLC (57) ABSTRACT

An allergy preventive or itching preventive food containing persimmon leaves or a persimmon leaf extract, a persimmon leaf extract-containing cosmetic composition having the action of improving allergic rough skin conditions or alleviating itching, an allergy or itching preventive or therapeutic composition.

3 Claims, 4 Drawing Sheets

ANTIALLERGIC COMPOSITION AND ANTIPRURITIC COMPOSITION

FIELD OF THE INVENTION

The present invention relates to articles containing a persimmon leaves or persimmon leaf extract. Specifically, the present invention relates to an allergy preventive food, a cosmetic composition having the action of improving rough skin conditions, an allergy preventive or therapeutic composition, an itching preventive food, a cosmetic composition having the action of alleviating itching and an itching preventive or therapeutic composition.

PRIOR ART

Persimmon (*Diospyros kaki L.*) is a deciduous tree of Chinese origin and belongs to Family Ebenaceae. The leaves of persimmon plants are included in herbs in a broad sense and called "Persimmon Leaf".

The persimmon leaf extract is known to be effective against arteriosclerosis and hypertension and have diuresis, antipyresis and hemostasis effects.

On the other hand, some galenicals are known to have antiallergic action. For example, FRAGRANCE JOURNAL 1995–10, pages 96–102 describes galenicals having antiallergic action and mentions "persimmon extract". Concerning the "persimmon extract", the portion used for extraction is not described in the above document, but kaki calyx is usually used to obtain persimmon extracts in the field of galenicals.

The object of the present invention is to provide an allergy preventive food, a cosmetic composition having the action of improving rough skin conditions, an allergy preventive or therapeutic composition, an itching preventive food, a cosmetic composition having the action of alleviating itching and an itching preventive or therapeutic composition.

DISCLOSURE OF THE INVENTION

One of the present inventors has drunk persimmon leaf tea for health promotion. He noticed in spring the year before last that the symptoms of pollinosis which had been presented in the past several years were eased.

In view of this fact, the present inventors conducted screening tests on allergy, especially pollinosis and atopic dermatitis, and found that the persimmon leaf extract has antiallergic action. The present inventors further found that the persimmon leaf extract has the action of reducing IgE level and is useful for alleviation of itching. The present invention has been accomplished based on these findings.

The present invention provides the items listed below.
1. A food containing persimmon leaves or a persimmon leaf extract.
2. A food of item 1 which is an allergy preventive food.
3. A food of item 1 which is an atopy preventive food.
4. A food of item 1 which is an itching preventive food.
5. A cosmetic composition containing a persimmon leaf extract.
6. A cosmetic composition of item 5 having the action of improving allergic rough skin conditions.
7. A cosmetic composition of item 5 having the action of improving atopic rough skin conditions.
8. A cosmetic composition of item 5 having the action of alleviating itching.
9. A pharmaceutical composition containing a persimmon leaf extract.
10. A pharmaceutical composition of item 9 which is an allergy preventive or therapeutic composition.
11. A pharmaceutical composition of item 9 which is an atopy preventive or therapeutic composition.
12. A pharmaceutical composition of item 9 which is an itching preventive or therapeutic composition.
13. A method for preventing or treating allergy, which comprises ingesting or administering an effective amount of persimmon leaves or a persimmon leaf extract.
14. A method of item 13 wherein the allergy is atopy.
15. A method for preventing or treating itching, which comprises ingesting or administering ingesting an effective amount of persimmon leaves or a persimmon leaf extract.
16. A method for improving allergic rough skin conditions, which comprises applying an effective amount of a persimmon leaf extract to the skin.
17. A method of item 16 wherein the allergy is atopy.
18. A method of alleviating itching, which comprises applying an effective amount of a persimmon leaf extract to the skin.

In the present specification, the term "persimmon" means any of the plants which belong to *Diospyros kaki L.*. Particularly, persimmons grown in Japan, Korea and China are preferable.

1. Food

The food of the present invention includes an allergy preventive food and an itching preventive food. The food of the present invention also includes an IgE level reducing food.

The allergy preventive food of the present invention can be used for preventing various allergic diseases, for example atopic dermatitis, bronchial asthma, allergic rhinitis, angioedema, food allergy and like atopy (atopic diseases), allergic contact dermatitis, pollinosis, urticaria, etc. It is especially useful for preventing pollinosis and atopy and most preferably used for preventing atopy, more specifically atopic dermatitis.

The itching preventive food of the present invention are valuable for preventing or suppressing itching caused by various factors, such as allergic contact dermatitis, atopic dermatitis, pollinosis, urticaria and other allergic diseases.

The IgE level reducing food is applicable to all diseases accompanied by IgE increase without limitation. Examples of diseases accompanied by IgE increase include atopic diseases (e.g., atopic dermatitis, bronchical asthma, allergic rhinitis, angioedema and food allegy), pollinosis and urticaria.

The persimmon leaf extract used for the food of the invention can be obtained by extracting persimmon leaves with a solvent usually used for extraction of plants. There is no specific limitation on the solvent, but an aqueous medium is preferably used. Examples of aqueous media include water, or a mixture of water and one or more other solvents such as methanol, ethanol, isopropanol or like lower alcohols or acetone. For extraction, use of water alone is particularly preferable.

Extraction is preferably conducted at the temperature about 0° C. to the boiling point of the solvent for about 10 seconds to about 24 hours. The ratio of the persimmon leaves to the solvent is not specifically limited to, but the solvent is used preferably in an amount of about 2 to about 1000 parts by weight of per part by weight of the persimmon leaves.

The persimmon leaf extract-containing solution obtained by the extraction may be used as it is or freeze dried to form a powder or concentrated to provide a concentrated extract, in accordance with the intended use.

Even when persimmon leaves per se or dried persimmon leaves are used, components included in the extract of persimmon leaves will be ingested. Therefore, the food of the invention may contain persimmon leaves as they are or may contain dried persimmon leaves.

The persimmon leaf extract or persimmon leaf content of the food of the invention can be selected from a wide range without limitation, as long as the desired effects are obtained. It is preferable for the content to be in the range of about 0.001 to about 80%, particularly about 0.01 to about 70%, on a dry weight basis of the extract (in this specification, "%" means "wt. %", unless otherwise specified).

The food of the invention may be prepared by mixing a persimmon leaf extract or persimmon leaves with food ingredients and additives according to conventional methods of the form. The food of the invention may be a persimmon leaf extract or persimmon leaves per se, not containing any food ingredients or additives.

The food of the invention may be in various forms. Examples of food forms are beverages (including health drinks) such as a persimmon leaf tea or drink containing an extract of persimmon leaves alone or with an extract of other tea leaves (e.g., green tea, oolong tea, tien-cha, black tea,); powdered beverages such as powdered juices and powdered soups; confectionery such as chocolates, candies, chewing gum, ice cream, jelly, cookies, biscuits, corn flakes, chewable tablets, gummi, wafers and senbei (Japanese rice crackers); seasonings such as dressings and sauces; breads, noodles, konnyaku (alimentary yam paste), kneaded products (e.g., fish cake); furikake (a mixture of dried fish and vegetable flakes for sprinking on steamed rice); and so on.

Among these food forms, beverages are preferable.

The food of the invention may contain food ingredients and additives usually incorporated in such form of food. Examples of additives include sweeteners, coloring agents, antioxidants, vitamins, aromatics or the like. These additives can be selectively used in accordance with the food form.

For preparing beverages, usable as ingredients are water, L-ascorbic acid etc.

For preparing powdered beverages, usable as ingredients are dextrin, aromatics etc.

The food of the invention may contain not only persimmon leaves but also other herbs (e.g., chamomile, ginger, rose hip, etc.).

The food of the invention may be used as a food ingredient to prepare a desired food. As a food ingredient, the food of the invention may be added to food articles that have been already prepared, for example, commercially available drinks.

The intake amount of the food is suitably selected in accordance with the food form, the person's age, sex and other conditions, but may be such that the daily intake amount of the persimmon leaf extract is usually in the range of about 5 to about 600 mg, preferably about 10 to about 300 mg, on a dry weight basis, per kg body weight for a human adult. The food can be ingested once a day or in 2–4 divided amounts a day.

The food of the invention, which has allergy preventive action, itching preventive action and IgE level reducing action can be used as health foods, functional foods, nutritional supplementary foods, foods for specified health use, foods for patients of specific disease etc.

The food of the present invention may also be used as domestic animal feeds or pet foods.

The domestic animal feed and pet food may be in any of the conventional forms. They can be prepared by mixing the persimmon leaf extract or persimmon leaves with food ingredients and additives usually incorporated in domestic animal feeds or pet foods according to conventional methods of the form. Of course, the persimmon leaf extract or persimmon leaves per se may be used as domestic animal feeds or pet foods.

The persimmon leaf extract or persimmon leaf content and intake amount of the feed or pet food can be suitably selected without limitation, as long as the intended effects of the invention are obtained. The content and the intake amount can be selected in accordance with the form, kind of domestic animal or pet, etc. and may be the same as in the case of the above food.

2. Cosmetic Composition

The cosmetic composition of the present invention includes a cosmetic compositions having the action of improving allergic rough skin conditions and a cosmetic compositions having the action of alleviating itching.

The cosmetic composition of the present invention having the action of improving allergic rough skin conditions can be used as a cosmetic composition for improving rough skin conditions caused by various allergic diseases.

Examples of allergic diseases are atopy, allergy contact dermatitis, urticaria and the like. The cosmetic composition of the invention is especially useful for improving rough skin conditions caused by atopy, more specifically atopic dermatitis.

The cosmetic composition of the present invention having the action of alleviating itching are valuable for suppressing itching caused by various factors, such as allergic contact dermatitis, atopic dermatitis, pollinosis, urticaria and other allergic diseases.

The extraction of persimmon leaf extract can be carried out in the same manner as mentioned above in the preparation of the food of the invention.

The persimmon leaf extract-containing solution obtained by the extraction may be used as it is or freeze dried to form a powder or concentrated to provide a concentrated extract, in accordance with the intended use.

The persimmon leaf extract content of the cosmetic composition of the invention can be selected from a wide range without limitation, as long as the desired effects are obtained. It is preferable for the extract content to be in the range of about 0.001 to about 80%, particularly about 0.01 to about 70%, on a dry weight basis.

The form of the cosmetic composition can be selected from various forms in accordance with the intended use.

Examples are soaps, facial cleaning preparations, skin lotions, milky lotions, foundations, lip colors, lip creams, cleansing creams, massage creams, packs, hand creams, hand powders, body shampoos, body lotions, body creams, bath cosmetics and the like.

The cosmetic composition of the invention can be used by a usual method in accordance with the form. The powdery cosmetics such as hand powder may be used by applying it to the inside of rubber gloves beforehand and wearing them.

The cosmetic composition of the invention contains a persimmon leaf extract as an essential ingredient and is formed into general cosmetics using suitable carriers.

The carrier used for the cosmetic composition of the invention can be selected from conventional carriers in accordance with the cosmetic form. Examples of carriers are binders, surfactants, moisturizing agents, fillers, extenders, wetting agents and like diluents or excipients.

The cosmetic composition of the invention may further contain antiseptics, colorants, preservatives, antioxidants, aromatics, etc., when necessary.

The cosmetic composition of the invention may contain not only persimmon leaf extract but also other extract of herbs conventionally incorporated in cosmetics, e.g., aloe extract and houttuynia extract.

The cosmetic composition of the invention can be prepared by a conventional method in accordance with the form.

As regards the cosmetic composition of the invention, the amount to be used is suitably selected in accordance with the cosmetic form, rough skin conditions, etc. The cosmetic composition may be applied to the skin in a suitable amount and once a day or in 2–4 divided amounts a day.

3. Pharmaceutical Composition

The pharmaceutical composition of the present invention includes an allergy preventive or therapeutic composition and an itching preventive or therapeutic composition. The pharmaceutical composition of the present invention also includes an IgE level reducing pharmaceutical composition.

The allergy preventive or therapeutic composition of the invention can be used for preventing or treating various allergic diseases, for example atopic dermatitis, bronchial asthma, allergic rhinitis, angioedema, food allergy and like atopy (atopic diseases), allergic contact dermatitis, pollinosis, urticaria, etc. It is especially useful for preventing or treating pollinosis and atopy and most preferably used for preventing or treating atopy, more specifically atopic dermatitis.

The itching preventive or therapeutic composition of the present invention is valuable for preventing or suppressing itching caused by various factors, such as allergic contact dermatitis, atopic dermatitis, pollinosis, urticaria and other allergic diseases.

The IgE level reducing pharmaceutical composition is applicable to all diseases accompanied by IgE increase without limitation. Examples of diseases accompanied by IgE increase include atopic diseases (e.g., atopic dermatitis, bronchical asthma, allergic rhinitis, angioedema and food allegy), pollinosis and urticaria.

The extraction of persimmon leaf extract can be carried out in the same manner as mentioned above in the preparation of the food of the invention.

The persimmon leaf extract-containing solution obtained by the extraction may be used as it is or freeze dried to form a powder or concentrated to provide a concentrated extract, in accordance with the intended use.

The persimmon leaf extract content of the preventive or therapeutic composition of the invention can be selected from a wide range without limitation, as long as the desired effects are obtained. It is preferable for the extract content to be in the range of about 0.001 to about 80%, particularly about 0.01 to about 70%, on a dry weight basis.

The preventive or therapeutic composition of the invention contains a persimmon leaf extract as an essential ingredient and is formed into general pharmaceuticals using suitable carriers.

The unit dosage form of the pharmaceutical composition can be selected from various forms in accordance with therapeutic purpose. Typical examples are solid preparations such as extracts, tablets, pills, granules, capsules and troches; powders such as powders for internal use and powders for external use; liquid preparations such as liquids, suspensions, emulsions, injections (liquids, suspensions, etc.), syrups, lotions, aerosols, ophthalmic solutions, infusions and decoctions; cream preparations such as ointments; cataplasms, etc.

Examples of pharmaceutically acceptable carriers used for the preventive or therapeutic composition of the invention are binders, disintegrators, surfactants, absorption promoters, moisturizing agents, adsorbents, lubricants, fillers, extenders, humectants and like diluents or excipients. These carriers are selectively used in accordance with the unit dosage form.

The preventive or therapeutic composition of the invention may further contain antiseptics, sweeteners, coloring agents, antioxidants, preservatives, aromatics, flavors, other medicine, etc. if necessary and may be formed into pharmaceuticals.

The pharmaceutical composition can be prepared by a conventional method in accordance with the intended pharmaceutical form.

There is no specific limitation on the method of administering the pharmaceutical composition. A proper administration such as oral administration or percutaneous administration can be selected in accordance with the dosage form, patient's age, sex and other conditions, severity of disease, etc. The parenteral injection is administered intravenously or by the intramuscular, intra-dermal, subcutaneous or intraperitoneal route. The aerosol may be used as a collunarium and administered through mucosa.

The administration method further includes the following methods. Medical masks are prepared by the dipping, coating or spraying step using a liquid preparation such as an infusion or a decoction, followed by drying the gauze masks, and patients (particularly, pollinosis patients) wear the masks. A powder is applied to the inside of rubber gloves beforehand and a patient wears the gloves.

The dosage of the pharmaceutical composition is suitably selected in accordance with the dosage form, patient's age, sex or other conditions, severity of disease, etc., but may be such that the daily intake of the persimmon leaf extract is usually in the range of about 5 to about 600 mg, preferably about 10 to about 300 mg, on a dry weight basis, per kg body weight for a human adult. The pharmaceutical composition can be administered once or in 2–4 divided doses a day.

BEST MODE FOR CARRYING OUT THE INVENTION

The following experiments are provided to illustrate the present invention, and are not intended to limit the scope thereof. All percentages are by weight unless otherwise specified.

REFERENCE EXAMPLE 1

Preparation of Persimmon Leaf Extract

Persimmon leaves, which obtained from the persimmon plant grown in China, were mixed with boiling distilled water (persimmon leaves:water=100:5 (by weight)) and stirred. The resulting extract solution was ice-cooled, subjected to suction filtration through filter paper and freeze-dried. The amount of the obtained extract (freeze-dried extract) was 0.004 g (0.4%) per milliliter of the extract solution and 0.06 g per gram of the leaves.

The obtained extract was used in the following experiments and Formulation Examples.

EXPERIMENT 1

Histamine Release Suppression Test Using Human Basophilic Leukemia Cell Line KU812

A human basophilic leukemia cell line KU812 was grown in a RPMI 1640 medium (GIBCO) supplemented with 10% fetal bovine serum (treated at 56° C. for 30 min), at 37° C. in 5% $CO_2$. The medium was washed by addition of a histamine release buffer (IMMUNOTECH) followed by centrifugation (1500 rpm, 5 min, 4° C.) and removal of the supernatant. The washing procedure was carried out twice. Then, a histamine release buffer was added to prepare a cell suspension having a cell density of $10^5$ cells/ml. 100 μl of the cell suspension and 100 μl of a histamine release buffer solution containing 0.02% persimmon leaf extract (test substance) or 0.02% epinephrine (reference substance) were placed in a 1.5 ml Eppendorf tube, and allowed to stand with ice-cooling for 30 minutes (final cell number: $10^4$, final concentration of test substance/reference substance: 0.01%). After centrifugation (1500 rpm, 5 min, 4° C.) and removal of the supernatant, the cells (precipitate) were resuspended in 200 μl of a histamine release buffer. 3 μl of CRA-1 (a high affinity IgE receptor antibody, COSMO BIO Co., Ltd.) solution (CRA-1 concentration: 1 mg/ml) was added to the suspension (final CRA-1 concentration:15 μg/ml), followed by 30-minute incubation at 37° C. After centrifugation (2000 rpm, 10 min, 4° C.), the histamine content of the supernatant was measured using a Histamine EIA Kit (IMMUNOTECH) (N=4). Then, the mean and standard deviation of the measured values were obtained from the calibration curve, and the histamine release suppression rate (%) was calculated according to the following equation:

$$\text{Histamine release Suppression rate (\%)} = 100 - \frac{A-B}{C-B} \times 100$$

wherein:
A represents the histamine content (n M) released from cells treated with the test substance/reference substance and CRA-1;
B represents the histamine content (n M) released from untreated cells; and
C represents the histamine content (n M) released from cells treated with CRA-1 only.

Figure 1:
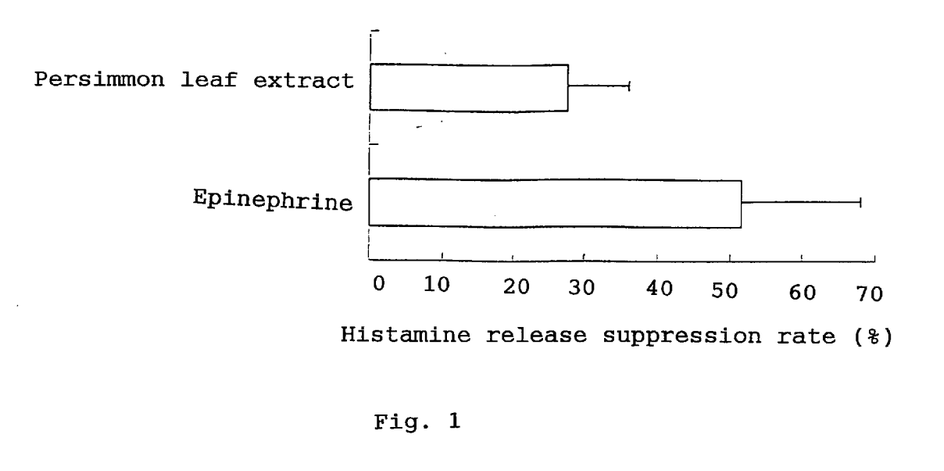
FIG. 1 shows the results of Experiment 1. It shows histamine release suppression effects of a persimmon leaf extract using human basophilic leukemia cell line (KU812).

FIG. 1 shows the results of histamine release suppression test of the persimmon leaf extract (test substance) and epinephrine (reference substance). The histamine release suppression rate of the persimmon leaf extract was 27±9%, and that of epinephrine was 52±16%. The results demonstrate that the persimmon leaf extract has histamine release suppression effect, like epinephrine known as a medicine.

EXPERIMENT 2

Suppression of Passive Cutaneous Anaphylaxis (PCA) in Mice

Twelve DDY male mice (4 wks old) were obtained from Japan SLC, and housed in cages (6 per cage) in a room at a temperature of 23±3° C. and a humidity of 55±15%, with a 12 h—12 h light-dark cycle (light on 7:00 to 19:00). The mice were preliminarily fed a standard diet (Labo MR Stock, Nihon Nosan Kogyo K. K.) for 3 days and divided into a test and a control group (6 per group).

A 5% (w/v) solution of the persimmon leaf extract in distilled water was forcedly administered (0.25 g/5 ml/kg) to the test group by the oral route using a metal stomach tube. To the control group, distilled water was forcedly administered (5 ml/kg) in the same manner.

One hour after the administration, 20 μl of an anti-DNP mouse IgE antibody (10 μg/ml) was intracutaneously injected from the right auricula and 20 μl of physiological saline from the left auricula. Twenty four hours after the intracutaneous injection, 100 μl of DNP-BSA (1 mg/ml) was intravenously injected from the tail. Thirty minutes thereafter, the thickness of the auriculae was measured with a thickness gauge (OZAKI SEISAKUSHO K. K.) three times, and the mean and standard deviation of the measured values were obtained. Then, the auricula swelling rate and auricula swelling suppression rate were calculated according to the following equations. The significant difference between the groups was determined by Student's t-test.

Auricula swelling rate (%) =
$$\frac{\text{Right auricula thickness} - \text{Left auricula thickness}}{\text{Left auricula thickness}} \times 100$$

Auricula swelling suppression rate (%) =
$$100 - \frac{\text{Mean swelling rate of test group}}{\text{Mean swelling rate of control group}} \times 100$$

Figure 2:
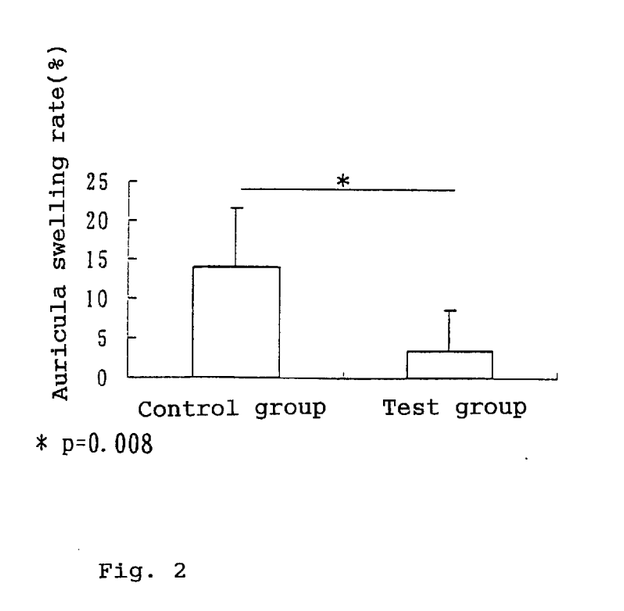
FIG. 2 shows the results of Experiment 2. It shows suppression effects of a persimmon leaf extract against passive cutaneous anaphylaxis (PCA) reactions in mice.

In the control group, the left auricula and right auricula thicknesses were 0.185±0.007 mm and 0.211±0.016 mm, respectively, hence the auricula swelling rate was 14.1±7.4%. On the other hand, in the test group, the left auricula and right auricula thicknesses were 0.197±0.020 mm and 0.204±0.025 mm, respectively, hence the auricula swelling rate was 3.5±5.2% (FIG. 2). That is, a significant auricula suppression of 75.5% (p=0.008) was achieved in the test group given the persimmon leaf extract.

EXPERIMENT 3

Suppression of Contact Dermatitis in Mice

ICR male mice (7 wks old) were obtained from Japan SLC, and divided into three groups: a test group (N=4) for continuous administration of the persimmon leaf extract for 5 days before sensitization (test group 1); a test group (N=5) for continuous administration of persimmon leaf extract for 5 days after sensitization (test group 2); and a control group for administration of distilled water for 5 days before sensitization and 5 days after sensitization. The persimmon leaf extract, in the form of a 5% (w/w) solution in distilled water, was forcedly administered (0.25 g/5 ml/kg/day) by the oral route using a metal stomach tube. Distilled water was administered (5 ml/kg/day) in the same manner. For sensitization, the mice were shaved, and on the same day or the following day, 0.1 ml of 0.5% (v/v) DNFB solution in ethanol was applied to the abdominal skin. Five days after the sensitization, 20 μl of 0.25% (v/v) DNFB solution in acetone/olive oil (4:1) was applied to the inner and outer surfaces of the left auricula to induce an allergic reaction. The left auricula thickness was measured before and 24 hours after inducement of the allergic reaction, using a thickness gauge (TECLOCK CORPORATION). The auricula swelling rate in each group and the auricula swelling suppression rate in each test group were calculated according to the following equations. The significant difference among the groups was determined by Student's t-test.

Auricula swelling rate (%) =

$$\frac{\text{(Left auricula thickness after inducement} - \text{Left auricula thickness before inducement)}}{\text{Left auricula thickness before inducement}} \times 100$$

Auricula swelling suppression rate (%) =

$$100 - \frac{\text{Mean swelling rate of test group}}{\text{Mean swelling rate of control group}} \times 100$$

Figure 3:
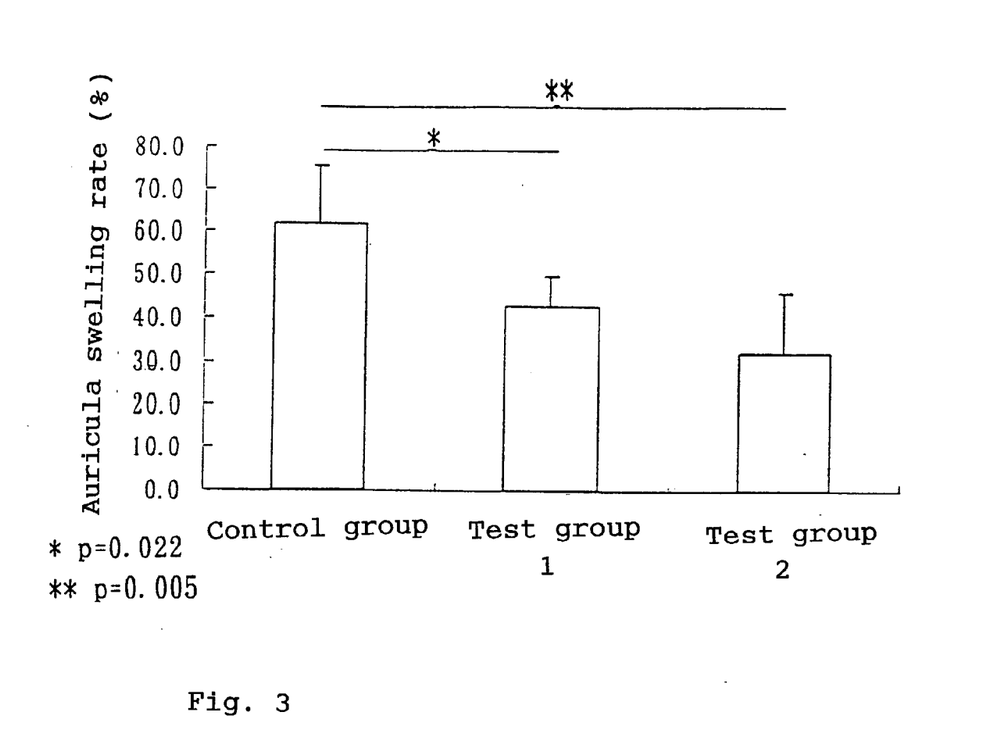
FIG. 3 shows the results of Experiment 3. It shows suppression effects of a persimmon leaf extract against contact dermatitis in mice.

The auricula swelling rate in the control group was 61.6±13.9, whereas the auricula swelling rates in the test groups 1 and 2 were 42.9±6.7% (p−0.022) and 32.5±13.6% (p=0.005), respectively (FIG. 3). Thus, in the test groups 1 and 2, the auricula swelling was suppressed by 30.4% and 47.2%, respectively, demonstrating that the persimmon leaf extract shows a significant auricula swelling suppression effect by administration either before or after sensitization.

Experiment 3 was conducted according to an experiment procedure generally employed for screening for pollinosis.

Of the above experiments, Experiments 1 and 2 are concerned with type I allergic reaction, and Experiment 3 with type IV allergic reaction. Accordingly, the results of the above experiments confirmed that the persimmon leaf extract is valuable for preventing diseases associated with these allergic reactions (e.g., atopic dermatitis, pollinosis, allergic contact dermatitis and urticaria), and for suppressing or alleviating symptoms of such diseases.

EXPERIMENT 4

Histamine Release Suppression Test Using Human Whole Blood

Since persimmon calyxes are generally used as a galenical, this experiment compared the histamine release suppression effect of a persimmon leaf extract and persimmon calyx extract at the same concentration.

Human whole blood was obtained from healthy volunteers and was added to heparin. A blood sample was prepared by adding 6 parts by weight of a histamine release buffer (IMMUNOTECH) to 1 part by weight of the heparinized human whole blood. 200 $\mu$l of the blood sample and 100 $\mu$l of a histamine release buffer solution containing 0.03% of the persimmon leaf extract (test substance) or 0.03% of a extract of persimmon calyxes extracted with dilute ethanol (comparison substance) or 0.03% of epinephrine (reference substance) were placed in a Eppendorf tube and allowed to stand for 30 minutes with ice-cooling (final concentration of the test substance/comparison substance/reference substance:0.01%).

Figure 4:
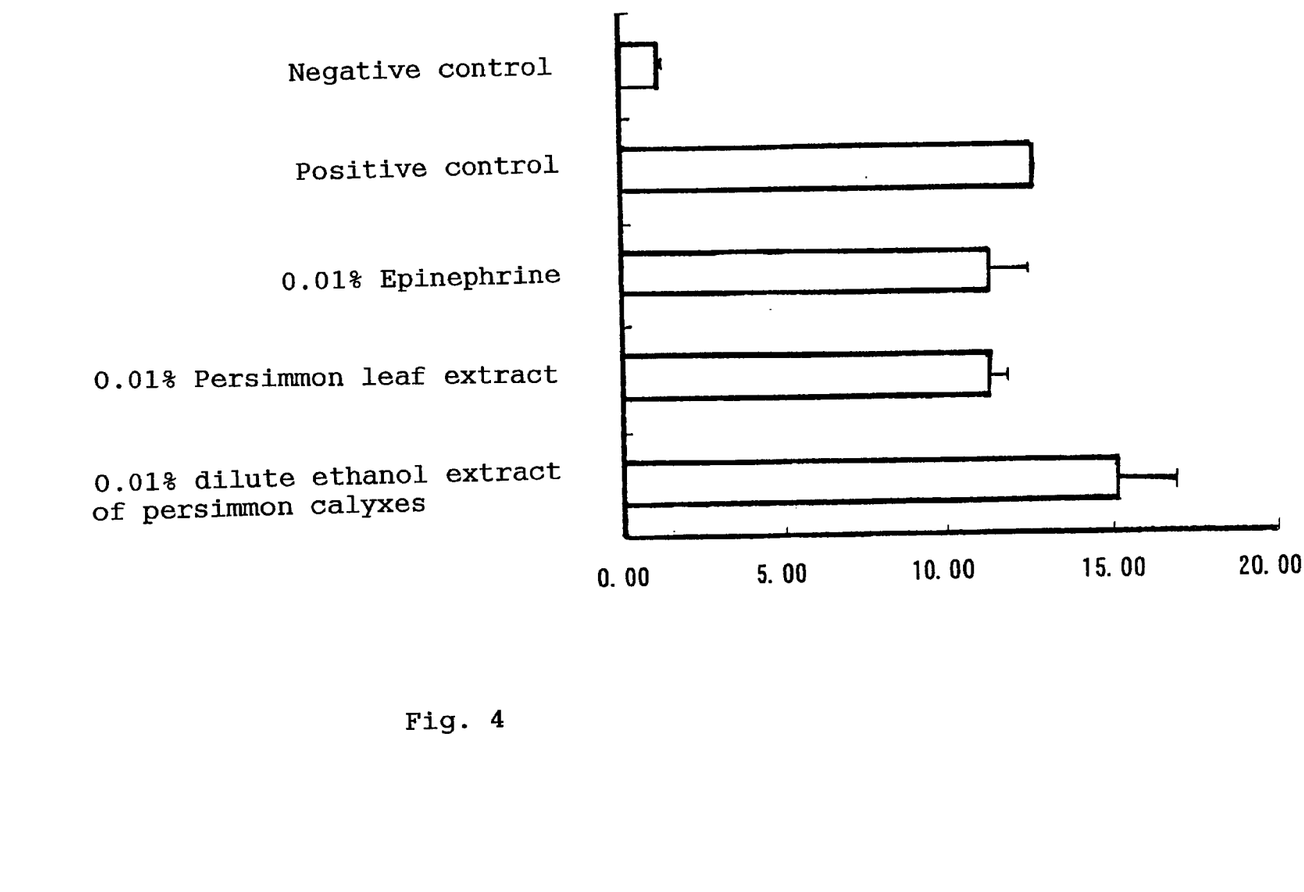
FIG. 4 shows the results of Experiment 4. It shows histamine release suppression effects of a persimmon leaf extract using human whole blood.

After centrifugation (3000 rpm, 5 min, 4° C.) and removal of the supernatant, the cells (precipitate) were resuspended in 300 $\mu$l of a histamine release buffer. 4.5 $\mu$l of CRA-1 (an antihuman FcεRI receptor antibody, COSMO BIO, at a concentration of 1 mg/ml) was added to the suspension (final CRA-1 concentration: 15 $\mu$g/ml), followed by 30-minute incubation at 37° C. After centrifugation (3000 rpm, 10 min, 4° C.), the histamine content in the supernatant was measured using a Histamine EIA Kit (IMMUNOTECH). The same experiments were conducted except for not adding test substance, comparison substance or reference substance (positive control: containing CRA-1 only), or except for not adding CRA-1, test substance, comparison substance or reference substance (negative control). The results are shown in FIG. 4.

The persimmon leaf extract (test substance) showed a histamine release suppression effect equivalent to that of epinephrine (reference substance) known as a medicine. On the other hand, the persimmon calyx extract (comparison substance), at the same concentration as of the persimmon leaf extract, showed no histamine release suppression effect.

EXPERIMENT 5

Intake Test Using NC/Nga Mice (Determination of Atopic Dermatitis Onset Rate and Serum IgE Level)

NC/Nga mice are conventional grade animals and atopic dermatitis model mice which spontaneously develop atopic dermatitis. The serum IgE level of the mice rises as atopic dermatitis develops.

Ten NC/Nga male mice (4 wks old) were obtained from Japan SLC, and housed in cages (5 per cage) in a room at a temperature of 23±3° C. and a humidity of 55±15%, with a 12 hr—12 hr light-dark cycle (light on 7:00 to 19:00). The mice were preliminarily fed a standard diet (Rabo MR Stock, Nihon Nosan Kogyo K. K.) for 7 days, and then divided into a test and a control group (5 per group), and fed the following diets ad libitum: Control group; a diet prepared by blending in a mixer a MF powder diet (ORIENTAL ENZYME K. K.) with 0.125 wt. % of α-corn starch (ORIENTAL ENZYME K. K.), Test group; a diet prepared by blending in a mixer the MF powder diet with 0.125 wt. % of the persimmon leaf extract.

The test group and control group were observed at the start (5 wks old) and end (13 wks old) of the test and at one-week intervals during the test, to confirm whether or not the mice developed atopic dermatitis.

All the mice in the control group developed atopic dermatitis, whereas four mice in the test group developed atopic dermatitis until the end of the test.

Figure 5:
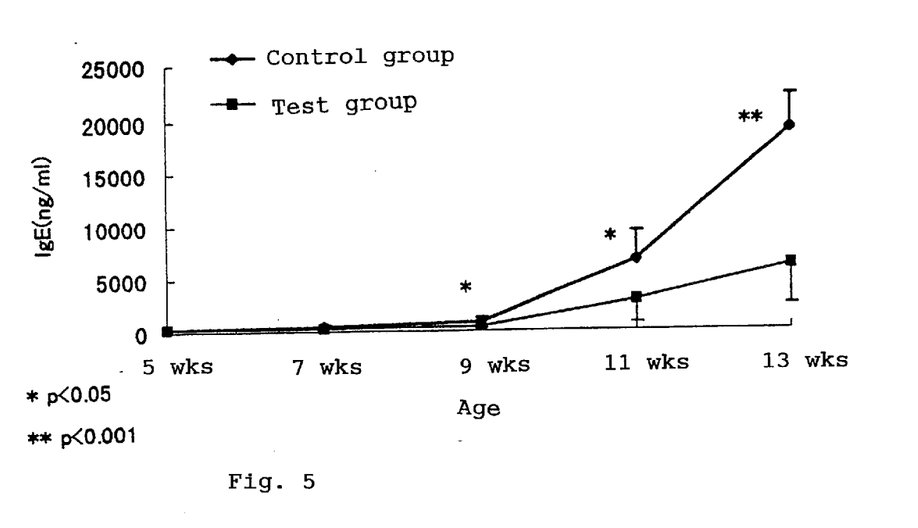
FIG. 5 shows the results of Experiment 5. It shows changes of the serum IgE level in NC/Nga mice with the lapse of time after the administration of a persimmon leaf extract.

The serum IgE level was determined using blood collected from the orbit of the mice of each group at the start and end of the test and at two-week intervals during the test, using a mouse IgE kit "YAMASA" EIA (Lot. 702). Then, the mean and standard deviation of the measured serum IgE level were obtained. The significant difference between the groups was determined by Student's t-test, with a significance level of 5% or less. The results are shown in FIG. 5.

In both groups, the serum IgE level gradually increased with age, from the age of 9 weeks. At the end of the test (13 wks old), however, the serum IgE level in the test group was 6,138 ng/ml whereas that in the control group was 19,190 ng/ml. That is, a significant serum IgE level reducing effect was achieved in the test group.

EXPERIMENT 6

Intake Test Using NC/Nga Mice (Scratching Movement Count)

NC/Nga mice are conventional grade animals and atopic dermatitis model mice which spontaneously develop atopic dermatitis and experience itching as the atopic dermatitis develops.

Ten NC/Nga male mice (4 wks old) were obtained from Japan SLC, and preliminarily fed in the same manner as in Experiment 5. After 7-day preliminary feeding, the mice were divided into a test and conrtol group (5 per group) and fed the same diets as in Experiment 5.

Figure 6:
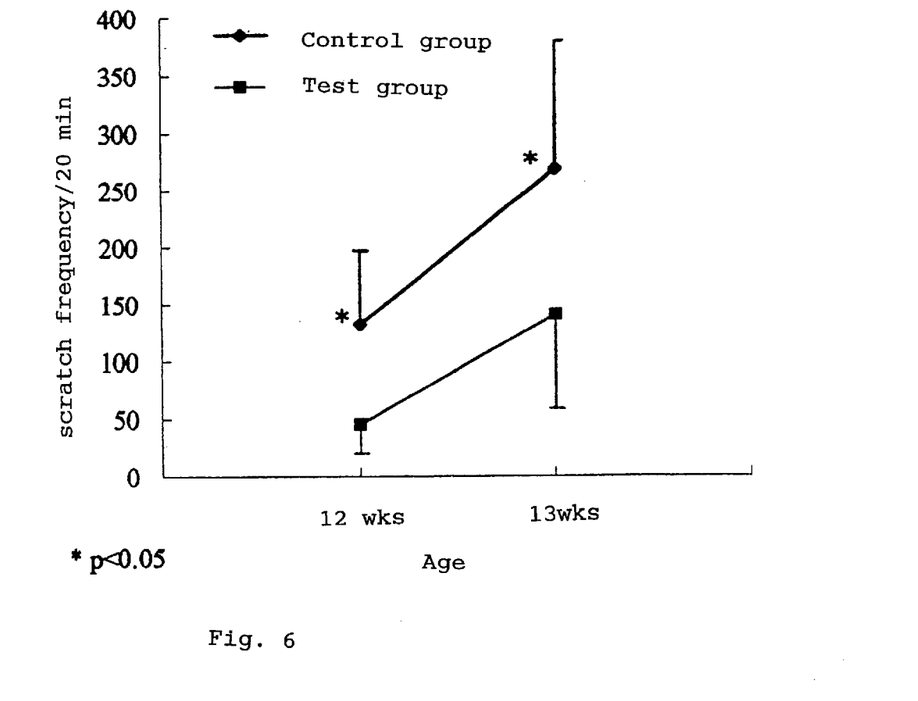
FIG. 6 shows the results of Experiment 6. It shows reduction in scratch frequency of NC/Nga mice by the administration of a persimmon leaf extract.

At the age of 12 weeks and at the end of the test, the number of scratching movements per 20 minutes was counted, and the mean and standard deviation of the count were obtained. The significant difference between the groups was determined by Student's t-test with significance level of 5% or less. The results are shown in FIG. 6.

The number of scratching movements per 20 minutes at the end of the test was 267±112 in the control group, and 141±83 in the test group. Thus, the scratching movements were significantly reduced in the test group. Also, at the age of 12 weeks, the number of scratching movements was significantly reduced in the test group.

Formulation Examples are given below. Each of the formulations was prepared in manners known in the art.

| Formulation Example 1: Chewable tablet | (mg) |
|---|---|
| Persimmon leaf extract | 500 |
| Xylitol | 300 |
| Aspartame | 4 |
| Magnesium stearate | 10 |
| Aromatic | 1 |

| Formulation Example 2: Chewing gum | (g) |
|---|---|
| Gum base | 20 |
| Powdered sugar | 60.5 |
| Starch syrup | 18 |
| Aromatic | 1 |
| Persimmon leaf extract | 0.5 |
| Total | 100 |

| Formulation Example 3: Ice cream | (g) |
|---|---|
| Concentrated milk | 30 |
| Fresh cream | 30 |
| Sugar | 15 |
| Emulsifier | 0.3 |
| Stabilizer | 0.5 |
| Aromatic | 0.3 |
| Egg extract | 1 |
| Persimmon leaf extract | 0.5 |
| Water | 22.4 |
| Total | 100 |

| Formulation Example 4: Chocolate | (g) |
|---|---|
| Cacao mass | 22 |
| Whole milk powder | 10 |
| Cacao butter | 19.9 |
| Lactose | 5 |
| Sugar | 40 |
| Aromatic | 0.1 |
| Egg extract | 1 |
| Persimmon leaf extract | 2 |
| Total | 100 |

| Formulation Example 5: Beverage | (g) |
|---|---|
| Persimmon leaf extract | 0.5 |
| L-ascorbic acid | 0.03 |
| Water | 99.47 |
| Total | 100 |

| Formulation Example 6: Powdered tea | (g) |
|---|---|
| Dextrin | 69 |
| Aromatic | 1 |
| Persimmon leaf extract | 30 |
| Total | 100 |

The persimmon leaf extract is effective against type I and type IV allergic reactions, and therefore foods, cosmetic compositions and pharmaceutical compositions containing the persimmon leaf extract or persimmon leaves are effective for preventing or treating such allergic reactions. Specifically, they are valuable for, for example, preventing allergic contact dermatitis, atopic dermatitis, pollinosis and urticaria, and suppressing or alleviating symptoms of such diseases.

Further, the persimmon leaf extract suppresses itching, for example, itching caused by atopic dermatitis.

What is claimed is:

1. A food product comprising a persimmon leaf extract obtained by extracting persimmon leaves with water or an aqueous solvent selected from the group consisting of mixtures of water and at least one of methanol, ethanol, isopropanol and acetone, the dry weight of the persimmon leaf extract being 5–80% of the total weight of the food product and in an amount for providing 5–600 mg (dry weight) of persimmon leaf extract per kg of body weight per day to effectively treat an allergy.

2. A food product comprising a persimmon leaf extract obtained by extracting persimmon leaves with water or an aqueous solvent selected from the group consisting of mixtures of water and least one of methanol, ethanol, isopropanol and acetone, the dry weight of the persimmon leaf extract being 5–80% of the total weight of the food product and in an amount for providing 5–600 mg (dry weight) of persimmon leaf extract per kg of body weight per day, to effectively treat atopic dermatitis.

3. A food product comprising a persimmon leaf extract obtained by extracting persimmon leaves with water or an aqueous solvent selected from the group consisting of mixtures of water and least one of methanol, ethanol, isopropanol and acetone, the dry weight of the persimmon leaf extract being 5–80% of the total weight of the food product, and in an amount for providing 5–600 mg (dry weight) of persimmon leaf extract per kg of body weight per day to effectively treat itching caused by allergic disease.

* * * * *